United States Patent [19]

Bedding

[11] Patent Number: 5,042,427
[45] Date of Patent: Aug. 27, 1991

[54] STORAGE OF ENTOMOPATHOGENIC NEMATODES

[75] Inventor: Robin A. Bedding, Hobart, Australia

[73] Assignee: Commonwealth Scientific and Industrial Research, Australia

[21] Appl. No.: 444,172

[22] PCT Filed: May 5, 1988

[86] PCT No.: PCT/AU88/00127
§ 371 Date: Jan. 5, 1990
§ 102(e) Date: Jan. 5, 1990

[87] PCT Pub. No.: WO88/08668
PCT Pub. Date: Nov. 17, 1988

[30] Foreign Application Priority Data

May 5, 1987 [AU] Australia ............... PI1743/87

[51] Int. Cl.$^5$ ............................... A01K 67/033
[52] U.S. Cl. .................................... 119/6.7
[58] Field of Search ........................ 119/1, 15

[56] References Cited

U.S. PATENT DOCUMENTS 4,334,498  6/1982  Bedding ................. 119/1
4,765,275  8/1988  Yukawa et al. .......... 119/1 X

FOREIGN PATENT DOCUMENTS 8700003  1/1987  PCT Int'l Appl. ........ 119/1
1086386  4/1984  U.S.S.R. ................ 119/1

Primary Examiner—Robert P. Swiatek
Attorney, Agent, or Firm—Sughrue, Mion, Zinn, Macpeak & Seas

[57] ABSTRACT

To transport entomopathogenic nematodes, it is necessary to store them in a manner such that a significant proportion of them survive after being stored and are reactivated when dispersed in water. The present invention provides storage by mixing an aqueous cream of clean third stage infective juveniles (J3) of nematodes with clay. The clay may be in chip form, or calcined, milled and sieved, but comporises from about 33 percent (by weight) to 67 percent (by weight) of the homogeneous mixture. Alternatively a layer of the aqueous cream may be placed on a layer of clay, then covered with another layer of clay. In another variation of the invention, the nematode cream is spread on an absorbent substrate which is then placed on a layer of clay while the relative humidity is reduced to 60 percent, to dry the nematode cream. Preferred clays are attapulgite clays, diatomaceous clays and kieselguhr. The nematodes are preferably of the family Steinernematidae or Heterorhabditidae.

13 Claims, 1 Drawing Sheet

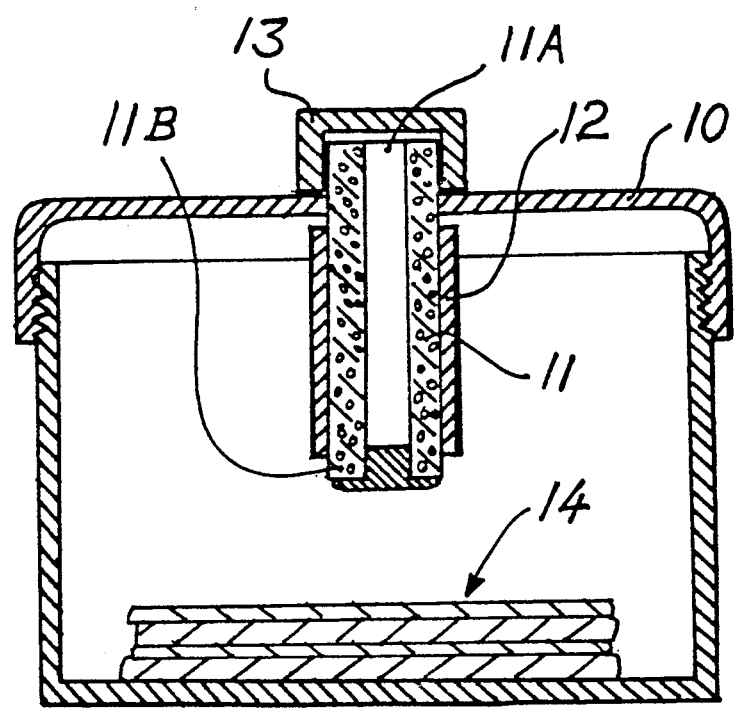

STORAGE OF ENTOMOPATHOGENIC NEMATODES

TECHNICAL FIELD

This invention concerns the storage of entomopathogenic nematodes. More particularly, it concerns the storage and transport of the third stage infective juveniles of nematodes.

BACKGROUND

It is becoming increasingly apparent that entomopathogenic nematodes in the families Steinernematidae and Heterorhabditidae have considerable potential for the control of a variety of pest insects. Infective juveniles (J3) of these nematodes (which can survive for many months in the environment without feeding) are able to seek out insects, penetrate into an insect's haemocoel and there release specific symbiotic bacteria (Xenorhabdus species). The bacteria kill the insect within one to two days, and provide suitable conditions for nematode reproduction. R. A. Bedding has developed satisfactory methods for the large scale in-vitro mass rearing of these nematodes. His techniques have been described in, for example, the specifications of his U.S. Pat. Nos. 4,178,366 and 4,334,498, the specification of Australian patent No. 509,879, and his papers in *Nematologica*, volume 27, pages 109 to 114, 1981 (entitled "Low cost in vitro mass production of Neoaplectana and Heterorhabditis species (Nematoda) for field control of insect pests") and in *Annals of Applied Biology*, volume 104, pages 117 to 120, 1984 (entitled "Large scale production, storage and transport of the insect-parasitic nematodes Neoaplectana spp. and Heterorhabditis spp."). However, bulk, high density storing and transport of the nematodes has remained a problem.

In the *Annals of Applied Biology* paper noted above, Bedding described the use of crumbed polyether polyurethane foam as a carrier for stored nematodes in polyethelene bags. Unfortunately, nematodes stored in this way required constant forced aeration, extraction of the nematodes from the foam took one to two hours and the method was not suitable for the storage of Heterorhabditis species. T. Yukawa and J. M. Pitt, in the specification of International patent application No. PCT/AU85/00020, have described various methods of storing nematodes. Some of the information in that specification is based on previously published work and some results are not repeatable. However, one technique disclosed in that specification is certainly original, and works well for one species of nematode. That technique involves the storage of infective juvenile nematodes with powdered activated charcoal. The nematodes are then able to survive at high densities under anaerobic or substantially anaeroebic conditions for considerable periods of time. However, that method has a number of serious disadvantages, namely:

a) It works satisfactorily only with the species *Steinernema feltiae.* b) Activated charcoal is extremely unpleasant to handle and packaging must take place in a fume cupboard. Recipients of nematodes packaged in this way also find the charcoal unpleasant to handle.

c) Activated charcoal is expensive.

d) The nematodes die within a few days if packages are exposed to temperatures higher than about 15° C. (probably as a result of increased nematode activity depleting oxygen).

e) Problems arise if the packages contain more than about 60 million nematodes.

f) There are constraints on the thickness of packages, largely because nematodes survive well when mixed with charcoal only if there is a central mass of nematodes surrounded by an outer layer of charcoal, which does not occur in thick packages.

DISCLOSURE OF THE PRESENT INVENTION

It is an object of the present invention to provide methods superior to those previously utilised or proposed for the storage and transport of entomopathogenic nematodes for commercial purposes.

This objective is achieved by using clay. The clay is used (a) to form a homogenous mixture of nematodes and the clay (the first aspect of the present invention); (b) to form a sandwich consisting of two layers of clay with a layer of nematode cream between them (the second aspect of the present invention); or (c) to slowly dry out the nematode cream (the third aspect of the present invention).

The benefits of using clay as a matrix or substrate material to store nematodes are believed to be threefold. Firstly, it is believed that the infective juveniles (J3) of the nematode genera Steinernema and Heterorhabditis survive for considerably longer periods of time when stored so that their movement is more or less constrained and they do not therefore utilise nearly as much energy as when they are moving, thus conserving stored food reserves. Such constraint can be obtained with clay. Secondly, it is believed that excretory products produced by the nematodes themselves may be toxic to the nematodes, but these products are likely to be adsorbed in the clay. Thirdly, it is believed that when nematodes (in general) are exposed to relative humidities of less than one hundred per cent, they respond physiologically so that, for instance, trehalose and inositol are produced (these sugars are known to confer some protection from the effects of further drying) and the nematodes enter a resting phase often accompanied by coiling of the body and limitation of movement. Utilisation of a clay substrate for nematode storage will produce this effect.

In the third aspect of the present invention, the desiccating effect of dry clay is utilised to slowly dry the nematodes well past the stage mentioned above so that they lose much of their internal water but may be rehydrated later to return to activity without significant mortality occurring. This method has the advantage of stopping respiration of the nematodes (and, of course, their movement) and greatly reducing all enzymatic activity. In addition, at low water activity, all growth of spoilage organisms is prevented. This application of the present invention thus has the potential to enable J3 nematodes to be stored for long periods, perhaps for several years. However, it should be noted that storage for prolonged periods has not been tested yet.

Nematodes stored in clay (either in the homogeneous combination form or as a sandwich) can be reactivated by dispersing the nematodes and clay in water. When the nematodes have been slowly dried out by clay, they are most effectively reactivated by first holding the nematode and clay combination in an atmosphere having a relative humidity of one hundred per cent but an absence of free water, then dispersing the nematodes in water.

Thus, according to the present invention, a method of storing third stage infective juveniles (J3) of nematodes comprises forming a homogeneous mixture of an aqueous concentrate (cream) of clean J3 nematodes with clay, the clay comprising from about 33 per cent (by weight) to about 67 per cent (by weight) of the mixture.

Also according to the present invention, a method of storing third stage infective juveniles (J3) of nematodes comprises placing a thin layer of an aqueous cream of clean J3 nematodes on a first layer of clay, then covering the nematode layer with a second layer of clay.

Further according to the present invention, a method of storing nematodes (which involves slowly drying out a cream of clean J3 nematodes) comprises the steps of a) spreading a layer of an aqueous cream of clean J3 nematodes on an absorbent substrate;

b) placing the absorbent substrate on a layer or bed of dry clay (that is, clay that has been stored at ambient humidity);

c) holding the combination of nematode cream, substrate and clay in an environment having a relative humidity of about 95 per cent for a period of at least three days; then d) subsequently reducing the relative humidity of the environment in which the combination is located over a period of several weeks, until the relative humidity reaches a value of about 60 per cent.

Nematodes/clay combinations store the nematodes independently of whether the combination is subsequently retained in an anaerobic environment or in an environment which contains a significant percentage of oxygen (such as air). In fact, completely anaerobic storage conditions are not preferred, for it has been found that the viability of the stored nematodes deteriorates much more rapidly, particularly at temperatures much above 10° C., in the absence of oxygen. Levels of oxygen in excess of about 2 per cent are desirable in the storage environment but levels well below the oxygen content of air are certainly not detrimental to the survival of the nematodes.

It has been discovered that when certain clays are combined with J3 entomopathogenic nematodes and most of the surface water has been removed from the combination, there is a greatly improved longevity after storage of the nematodes over a wide range of temperatures. Furthermore, the nematodes after such storage can be readily suspended in water simply by mixing the combination with water whereupon the suspension can be applied directly to soil or plants for the control of insects. Among the various clays that have been found to provide improved storage for these nematodes, those belonging to the group known as attapulgite clays give considerably better storage than others tested. However, diatomaceous clays and kieselguhr are amongst those materials which, when used in the present invention, give much improved storage over prior methods.

The storage method of the present invention has been successfully tested with most of the known species of entomopathogenic nematodes including: *Steinernema feltiae* (previously known as *Neoaplectana carpocapsae;* for the purpose of this specification all reference to Steinernema is as a synonym of Neoaplectana), *Steinernema bibionis, Steinernema glaseri, Steinernema affinis, Steinernema anomali, Heterorhabditis heliothidis, Heterorhabditis bacteriophora, Heterorhabditis megidis* and six further as yet undescribed new species of Steinernema from Australia, China and USA, two new species of the new genus of steinernematid from Australia, and four as yet undescribed new species of Heterorhabditis from, respectively, Australia, China, Cuba and Europe. All species of entomopathogenic nematodes which were tested proved to be amenable to storage in this way. Thus, since these species belong to two distinct families of nematodes (Steinernematidae and Heterorhabditidae) and include nearly all the species found therein, it seems clear that all such nematodes can be stored in this way.

A detailed description of the way in which nematodes are prepared for storage in a nematode and clay combination, and examples of realisations of the present invention will now be described.

PREPARATION OF THE NEMATODES PRIOR TO STORING

The manner in which the nematodes are processed prior to their combination with clays has an important influence on their further longevity. Obviously, if nematodes are exposed to adverse conditions such as high temperature, anoxia, exposure to pathogens or bacterial toxins, or mechanical or chemical damage, their longevity may be reduced. Apart from these factors, utilisation by the nematodes of their internal food reserves prior to storing should be reduced to a minimum. Also, it is important that the nematodes are as clean as possible when added to the clays so that microbial degeneration of the whole mixture is not encouraged.

All the nematodes used in the trials conducted to confirm the efficacy of the present invention were reared by the methods described in the two aforementioned papers by R. A. Bedding, or by modifications of those methods. However, the nematodes may be reared on insects in vivo or in liquid culture, provided the nematodes are free from appreciable amounts of extraneous matter remaining from the culture medium and are relatively free from nematode stages other than J3 (preferably no adult nematodes are present and certainly no more than 2 per cent of the nematodes should be adults). Extraction of the nematodes from a solid culture media was as described in the aforementioned 1984 paper by R. A. Bedding, or by a modified form of that technique, and washing was by sedimentation in tanks followed by decanting off the water. Nematodes were maintained in the tanks for two days after preliminary washing to allow for bacterial degradation of small particles of medium not removed by previous sedimentation, but during this period the nematodes in water suspension were aerated using a compressor. This period of aeration also helps to reduce populations of adult and other non-J3 stages, which have an adverse effect on storability.

After further washing, the nematodes were sedimented, the excess water was drained off and the sediment of nematodes was then pumped from the tanks into sieves lined with cloth which allowed the water, but not the nematodes, to pass through. Water was drained off in this way. In some trials, further water was removed by gathering up the cloth edges to encompass the nematode mass before squeezing out more of the remaining water. The resulting concentrate (cream) of nematodes contained from 0.5 to 3 million J3 nematodes per gram depending upon the species involved and the amount of inter-nematode water remaining.

These procedures were adopted for most of the trials undertaken although in some cases 0.1 per cent formaldehyde was added to the nematode concentrate prior to cloth sieving in order to stabilise, by cross linking, any remaining particles of rearing medium which would otherwise encourage the growth of contaminatory microorganisms.

In addition, a container, which has been designed by the present inventor for holding stored entomopathogenic nematodes and for slowly re-hydrating the stored nematodes when they are to be revived, will be described with reference to the accompanying drawing which is a partly schematic, vertical sectional view of an embodiment of such a container.

COMBINING NEMATODES AND CLAY SUBSTRATE

In general, to disperse the nematode cream in the clay matrix or substrate, the nematode cream was weighed and from one half to twice this weight of clay substrate was thoroughly mixed into the cream to produce a homogeneous mixture. The mixing was most satisfactorily accomplished by carefully kneading the clay and nematode cream by hand, continually breaking up any clumps of nematodes or clay in the process. Usually, some of the clay was not mixed with the nematode cream initially, for the water activity of the resulting mixture is of importance. The water activity of the initial mix was established at as near to 0.99 as possible before more clay was added (if lower water activity was required). The water activity was continually monitored during mixing using an electronic probe. With clay in the form of chips, from two to four hours were allowed to elapse after making the initial mixture before the water activity was adjusted by adding more clay, because equilibration of water content between the inside and outside of the chips is not instantaneous. With ground or powdered attapulgite clays, it was not necessary to allow more than a few minutes for equilibrium to occur. As operators became skilled at mixing the nematode cream and clay, there was a minimal requirement for repeated use of the probe.

After mixing the nematode creams with clays, the resultant combinations were left at 15° C. for four hours (initial nematode activity and heat of absorption cause a rise in temperature) and were then stored in a variety of containers ranging from polyethelene bags, glass jars, vials or tubes, plastic food or other containers, waxed cardboard cartons or aluminium boxes. In some instances, the nematodes and clay combinations were wrapped in aluminium foil or plastic (polyethelene or polypropylene) food wrap. If a package of nematodes and clay combination was not to be stored under refrigeration, some provision was made for gaseous exchange between the interior and the exterior of the package (while minimising water loss) so that anaerobic conditions did not develop within the containers.

Having broadly described the techniques used to perform the present invention, particular examples of the invention will now be described, by way of illustration.

EXAMPLE 1

A. 3.2 kilograms of cream comprised of approximately 6000 million J3 Steinernema feltiae All strain, produced as outlined above but not having had water actively squeezed from it, were placed in a plastic container (a fish basket). 3.2 kilograms of calcined chips of attapulgite clay were carefully mixed in by hand to produce, as nearly as possible, a homogenous mixture. The mixture, some 10 cm deep inside the plastic container, was covered by aluminium foil to reduce drying, and left at 15° C. for four hours, being remixed after two hours. The nematodes/clay mixture was then packaged in twenty 200 g lots and twenty-four 100 g lots inside round, 500 ml and 250 ml plastic food containers. Each container was about 9/10 full and therefore had a small air space at the top. The wall of each container was perforated with 10 holes of about 2 mm diameter, evenly distributed around the container and adjacent to its upper rim. These perforations formed connections between the external environment and the air space at the top of the container. Eight of each size of container were held at 4° C. and four of each size of container were held at each of 15° C., 23° C. and 28° C. Two 100 g lots were placed at each of −8° C. and −18° C. Every two weeks (except, as seen from Table 1, in the case of containers stored at 4° C.), the total contents of one container from each temperature was added to water, left for five minutes and then stirred so that all of the nematodes from the container were suspended in water. The nematodes and smaller particles of attapulgite clay were then decanted off (leaving the larger particles as a sediment) and counted after sample dilution. The results are recorded in Table 1.

B. Two kilograms of cream comprised of approximately 3800 million Steinernema bibionis were treated as for A but the product nematodes/clay combination was packaged as 100 g lots in each of forty 250 ml containers. The containers were then stored at the same temperatures as those used in A and were sampled in the same manner. The results are also recorded in Table 1.

C. Two kilograms of Heterorhabditis heliothidis NZ strain were treated as in B, except that eight packages were left at 15° C. and only four at 4° C. (previous experiments having indicated poor survival of the nematodes that had been stored at 4° C.) The stored combinations were again sampled at intervals of two weeks, the results also being given in Table 1.

TABLE 1

Percentage survival of Steinernema and Heterorhabditis spp. after storage on calcined attapulgite chips at various temperatures

| Nematode Species | Storage Temp. | % J3 survival after storage times of | | | | | | | |
|---|---|---|---|---|---|---|---|---|---|
| | | 2 w | 4 w | 6 w | 8 w | 10 w | 12 w | 16 w | 24 w |
| S. felt. | 4° C. | 95 | 92 | 92 | 90 | 90 | 90 | 85 | 72 |
| S. felt. | 15° C. | 94 | 90 | 90 | 84 | — | — | — | — |
| S. felt. | 23° C. | 95 | 85 | 78 | 56 | — | — | — | — |
| S. felt. | 28° C. | 86 | 82 | 43 | 0 | — | — | — | — |
| S. felt. | −8° C. | 65 | 65 | — | — | — | — | — | — |
| S. felt. | −18° C. | 8 | 0 | — | — | — | — | — | — |
| S. bib. | 4° C. | 98 | 95 | 95 | 95 | 90 | 92 | 80 | 80 |
| S. bib. | 15° C. | 97 | 92 | 90 | 88 | — | — | — | — |
| S. bib. | 23° C. | 94 | 87 | 82 | 76 | — | — | — | — |
| S. bib. | 28° C. | 82 | 75 | 68 | 45 | — | — | — | — |
| H. NZ | 4° C. | 23 | 0 | 0 | 0 | — | — | — | — |

TABLE 1-continued

Percentage survival of Steinernema and Heterorhabditis spp. after storage on calcined attapulgite chips at various temperatures

| Nematode Species | Storage Temp. | % J3 survival after storage times of | | | | | | | |
|---|---|---|---|---|---|---|---|---|---|
| | | 2 w | 4 w | 6 w | 8 w | 10 w | 12 w | 16 w | 24 w |
| H. NZ | 15° C. | 95 | 95 | 95 | 92 | 90 | 83 | 80 | 80 |
| H. NZ | 23° C. | 97 | 90 | 92 | 85 | — | — | — | — |
| H. NZ | 28° C. | 92 | 89 | 85 | 74 | — | — | — | — |

Smaller amounts of all these species and a number of other species were tested in various types of containers, usually with results not significantly different from those listed in Table 1. However, steinernematids stored at temperatures above 15° C. in sealed polyethelene bags had rather poor survival compared with those stored in other containers.

Utilising the technique described in the paper by R. A. Bedding, A. S. Molyneux and R. J. Akhurst entitled "Heterorhabditis spp., Neoaplectana spp. and *Steinernema kraussei*: Interspecific and intraspecific differences in infectivity for insects", published in *Experimental Parasitology*, volume 55, pages 249 to 255, 1982, the infectivities of those nematodes remaining viable in the longest left samples were measured against mature blow fly (*Lucilia cuprina*) larvae. The infectivities were found to be similar to those of freshly harvested nematodes.

EXAMPLE 2

A. Two kilograms of *Steinernema feltiae* All comprising about 4000 million J3 nematodes were derived and creamed as described in Example 1, and were then mixed with 1.5 kilograms of milled calcined attapulgite clay which had been sieved through a 40 mesh (BSS) sieve. The Pf value of the resulting mixture was measured at 4.7. Thirty-five lots of 100 g of the resulting combination were stored in respective waxed cardboard cartons which were perforated as in Example 1, then held at 28° C., 23° C., 15° C. and 4° C. and examined at weekly intervals.

B. One kilogram of *Steinernema glaseri* NC 34 strain comprising about 1200 million J3 nematodes was mixed as for A but with 0.75 kilogram of the milled and sieved attapulgite clay. Eight lots of 200 g of the combination were stored in respective 500 ml plastic containers and four of these containers were held at 28° C. and four were held at 23° C. Samples were tested at intervals of one week, the results being included in Table 2.

C. One kilogram of *Heterorhabditis heliothidis* C1 strain comprising some 1500 million J3 nematodes was mixed with 0.75 kilogram milled and sieved attapulgite clay. Eight lots of 200 g of the combination were stored in respective 500 ml plastic containers and four of these were held at 23° C. and four were held at 15° C. The stored samples were examined periodically as described in Example 1. The percentage survival data for the J3 nematodes are presented in Table 2.

TABLE 2

Percentage survival of *Entomopathogenic nematodes* after storage in milled attapulgite at various temperatures

| Nematode Species | Storage Temp. | % J3 survival after storage times of | | | | | | | |
|---|---|---|---|---|---|---|---|---|---|
| | | 1 w | 2 w | 3 w | 4 w | 6 w | 12 w | 16 w | 24 w |
| S. felt. | 4° C. | 85 | 82 | 75 | 72 | — | — | — | — |
| S. felt. | 15° C. | 85 | 80 | 70 | 64 | — | — | — | — |
| S. felt. | 23° C. | 83 | 78 | 72 | 62 | — | — | — | — |
| S. felt. | 28° C. | 84 | 72 | 65 | 43 | — | — | — | — |
| S. glas. | 23° C. | 93 | 89 | 85 | 77 | — | — | — | — |
| S. glas. | 28° C. | 86 | 82 | 74 | 65 | — | — | — | — |
| H. hel. | 15° C. | — | 94 | — | 90 | — | 84 | — | 66 |
| H. hel. | 23° C. | — | 95 | — | 83 | — | 70 | — | 52 |

EXAMPLE 3

One kilogram of *Steinernema feltiae* Mexican strain J3 nematodes which had been concentrated in a cloth filter and then squeezed free of excess water was spread on a smooth surface to a depth of 2 cm and cut into blocks of about 100 g each. These blocks were each placed on a 2 cm deep bed of milled and calcined attapulgite clay within a 500 ml plastic container and covered with attapulgite clay so that a total of 50 g of attapulgite clay was in each container. A series of 2 mm diameter holes were made in the wall of the container near its rim. These nematodes were kept at 23° C. or 28° C. and had a lower mortality after one month than the stored nematodes and clay combinations of Example 2.

EXAMPLE 4

One kilogram of an aqueous cream of *Steinernema feltiae* All strain J3 nematodes was spread about 2 cm deep on filter paper lying over a bed of milled attapulgite clay and left until all the obvious interstitial water had been removed and the nematode mass was quite hard. The layer of nematodes on the filter paper was then placed on another 2 cm deep bed of milled attapulgite clay at the bottom of a sealable polystyrene box having walls 2.5 cm thick. The box was then sealed so that a relative humidity of about 95 per cent developed within the box and the nematodes slowly lost water over a period of several days. There could have been many layers in the polystyrene box in order to process larger quantities of nematodes and clay at the same time. As the nematodes dried, the amount of water vapour leaving them decreased and the relative humidity within the box gradually dropped. After two weeks, the relative humidity in the box was about sixty per cent and the water activity of the nematodes was, therefore, 0.6. No microbial growth could occur at such a low water activity; all nematode movement had ceased (thus conserving energy), and the nematodes required no oxygenation during storage. At this stage the nematodes could readily be revived by placing the dried mass of nematodes in water. Samples of the nematodes/clay (layered) combination were then stored in sealed containers. Each container had a bed of attapulgite clay with a water activity of 0.6 (attapulgite from the desiccating bed was used) covered by filter paper and then with a layer of the intermediate moisture-containing nematodes. Two months after storage at 23° C., approximately ninety per cent of the nematodes revived after being first placed in an environment of almost one hundred per cent relative humidity (but with no free water) for 24 hours.

The present inventor has developed a storage container for use with this Example of the present invention. One embodiment of such a container is illustrated in the accompanying drawing. As shown in the drawing, the container has a lid 10 through which a porous tube 11, open at its top 11a and closed at its lower end 11b projects. The porous tube is surrounded by a central wick 12, which descends from the lid into the container but not to the contents 14 (nematode/clay layers) of the container. The top of the porous tube is sealed by a cap 13 until the day before the nematodes are required for use. Then the seal (cap) is removed and the porous tub 11 is filled with water. The tube 11 has dimensions such that the wick becomes fully saturated without any free water dripping out on to the nematodes. With a saturated wick, the relative humidity in the container rises to one hundred per cent and the nematodes are very slowly hydrated (which is a prerequisite for maximum return to activity). The nematodes can then be dropped into water, where they revive within minutes and are ready for application.

Those skilled in this field will appreciate that although specific examples of the present invention have been described above, variations and modifications to the described embodiments can be made without departing from the present inventive concept.

What is claimed is:

1. A method of storing third stage infective juveniles (J3) of entomopathogenic nematodes, said method comprising forming a homogenous mixture of an aqueous cream of clean J3 entomopathogenic nematodes with clay, the clay comprising from about 33 per cent (by weight) to about 67 per cent (by weight) of the mixture.

2. A method as defined in claim 1, in which the mixing is effected by kneading the aqueous cream of nematodes with chips of the clay, and subsequently adjusting the water activity of the resultant mixture.

3. A method as defined in claim 2, including the step of monitoring the water activity of the mixture during the mixing of the clay and the nematode cream.

4. A method of storing third stage infective juveniles (J3) of entomopathogenic nematodes, said method comprising the steps of
    (a) placing a thin layer of an aqueous cream of clean J3 entomopathogenic nematodes on a first layer of clay, then
    (b) covering the layer of nematodes with a second layer of clay.

5. A method as defined in claim 4, in which the first layer of clay and the layer of cream each have a thickness of about 2 cm.

6. A method of storing third stage infective juveniles (J3) of entomopathogenic nematodes, said method comprising the steps of
    (a) spreading a layer of an aqueous cream of clean J3 entomopathogenic nematodes on an absorbent substrate;
    (b) placing the absorbent substrate on a layer or bed of dry clay;
    (c) holding the combination of nematode cream, substrate and clay in an environment having a relative humidity of about 95 per cent for a period of at least three days; and
    (d) subsequently, reducing the relative humidity of the environment in which the combination is held, over a period of several weeks, until it reaches a value of about 60 per cent.

7. A method as defined in claim 6, in which the absorbent substrate is a layer of filter paper.

8. A method as defined in claim 1, claim 4 or claim 6, in which the clay has been milled and sieved prior to its use in the method.

9. A method as defined in claim 1, claim 4 or claim 6 in which the clay is selected from the group consisting of attapulgite clays, diatomaceous clays and kieselguhr.

10. A method as defined in claim 1, claim 4 or claim 6 followed by the step of holding the product of the method in a container or wrapper which is impervious to air and water, at a temperature in the range from about 4° C. to about 28° C.

11. A method as defined in claim 10, in which said product is not to be stored under refrigeration, and the container or wrapper is perforated.

12. A method as defined in claim 1, claim 4 or claim 6 in which the nematodes are selected from the group of entomopathogenic nematodes consisting of the families Steinernematidae and Heterorhabditidae.

13. A method as defined in claim 1, claim 4 or claim 6 in which the maximum concentration of adult nematodes in the aqueous cream of J3 nematodes is 2 per cent.

* * * * *

UNITED STATES PATENT AND TRADEMARK OFFICE
CERTIFICATE OF CORRECTION

PATENT NO. : 5,042,427

DATED : August 27, 1991

INVENTOR(S) : Robin A. Bedding

It is certified that error appears in the above-identified patent and that said Letters Patent is hereby corrected as shown below:

Title page, item (73) should read--

Commonwealth Scientific and Industrial
Research Organization--.

Signed and Sealed this

Sixteenth Day of March, 1993

Attest:

STEPHEN G. KUNIN

*Attesting Officer*       Acting Commissioner of Patents and Trademarks